United States Patent [19]

Witiak et al.

[11] Patent Number: 5,071,872
[45] Date of Patent: Dec. 10, 1991

[54] METHOD FOR IMPROVING INTERLEUKIN-2 ACTIVITY USING ACI-REDUCTONE COMPOUNDS

[75] Inventors: Donald T. Witiak, Mt. Vernon; Pierre L. Triozzi, Columbus, both of Ohio

[73] Assignee: The Ohio State University Research Foundation, Columbus, Ohio

[21] Appl. No.: 567,266

[22] Filed: Aug. 14, 1990

[51] Int. Cl.$^5$ .................... A01N 43/30; A61N 37/66; C07K 3/00
[52] U.S. Cl. .................... 514/465; 514/889; 424/85.4; 424/85.7; 424/10; 530/351
[58] Field of Search ............... 514/461, 462, 464, 465, 514/889; 424/85.4, 85.2, 10

[56] References Cited

U.S. PATENT DOCUMENTS 3,585,214  6/1971  Boschetti et al. .................... 549/269
4,845,121  7/1989  Witiak et al. ........................ 514/454

FOREIGN PATENT DOCUMENTS 0259707  3/1988  European Pat. Off. .

OTHER PUBLICATIONS

Rosenberg, Important Advances in Oncology, pp. 55–91 (1986).
Ortaldo et al., J. Exp. Med., 164:1193 (1986).
Philips et al., J. Exp. Med., 161:814 (1986).
Parker et al., J. Immunol., 122:1572 (1979).
Remick et al., Biochem. Biophys. Res. Commun., 147:86 (1987).
Bermudez et al., J. Immunol., 140:3006–3013 (1988).
Frasier-Scott et al., J. Clin. Invest. 82:1877–1883 (1988).
Tilden et al., J. Leuk. Biol., 45:474–478 (1989).
Valitutti et al., Immunology, 67:44–50 (1989).
Klausner et al., Ann. Surg., 209:119–128 (1989).
Chouaib et al., Lymphokine Res., 7:237–245 (1988).
Parhar et al., J. Leuk. Biol., 44:474–484 (1988).
Lala et al., Cancer Res., 48:1072–1079 (1988).
Rappaport et al., J. Exp. Med., 155:943–948 (1982).
Rogers et al., Cell Immunol., 66:269 (1982).
Sosman et al., J. Natl. Cancer Inst., 80:1451–1461 (1988).
Eberlein et al., Arch. Surg., 124:542–547 (1989).
Seaman et al., J. Clin. Invest. 69:876–888 (1982).
Lipsky, J. Clin. Invest., 73:53–65 (1984).
Marcus et al., Cancer Res., 47:4028–4212 (1987).
Witiak et al., J. Med. Chem., 25:90–93 (1982).
Witiak et al., J. Med. Chem., 31:1437–1445 (1988).
Witiak et al., J. Med. Chem., 29:2170–2174 (1986).
Kamanna et al., Lipids, 1989, 24, 25–32.
Rao, Chem. Revs., 1976, 76, 625–694.
Pattenden, Fortschr. Chem. Org. Naturst., 1978, 35, 133–198.
Berdy, "Handbook of Antibiotic Compounds", CRC, Boca Raton, Fla., 1980, vol. II, p. 415.
Whitesell et al., J. Org. Chem., 1983, 48, 3548–3551.
Gore et al., J. Org. Chem., 1986, 51, 3700–3704.
Evans et al., Tetrahedron, 1988, 44, 5525–5540.
Helferich et al., Ber., 1937, 70, 465–468.
Wrobel et al., J. Org. Chem., 1983, 48, 3761–3764.
Bloomer et al., J. Org. Chem., 1974, 39, 113.
Ireland et al., J. Org. Chem., 1986, 51, 635–648.
Booth et al., J. Chem. Soc. Perkin Trans I, 1987, 121–129.
Brandange et al., J. Org. Chem. 1984, 49, 927–928.
Stork et al., J. Am. Chem. Soc., 1987, 109, 1564–1565.
Ireland et al., J. Org. Chem., vol. 44, 3041–3052 (1979).
Carey et al., Advanced Org. Chem., Part B, Second Edition, Plenum Press, New York, N.Y. (1983).
Vargaftig et al., J. Biochem. Pharmac., 30:263 (1981).

(List continued on next page.)

Primary Examiner—Jerome D. Goldberg
Assistant Examiner—T. J. Criares
Attorney, Agent, or Firm—Emch, Schaffer, Schaub & Porcello Co.

[57] ABSTRACT

A method for improving interleukin-2 induced lymphocyte killing of cancer cells comprises administering to a patient having cancer an effective amount of at least one aci-reductone compound containing a —C(OH)=C(OH)—C=O redox functionality or a physiologically acceptable salt thereof together with a physiologically acceptable carrier or excipient.

3 Claims, 4 Drawing Sheets

OTHER PUBLICATIONS

Ghosh, K. C., *J. Indian Chem. Soc.*, 24:323-326 (1947).

Schank, K., *Chem. Ber.*, 114:1958-1962 (1981).

Synthesis of Aci-Reductones as a New Class of Potential Hypolipidemic Agents, Kim et al., 18th Graduate Student Meeting in Medicinal Chemistry, Purdue University, Jun. 16-18, 1985.

Synthesis of Aci-Reductones as a New Class of Potential Hypolipidemic Agents, Kim et al., Biomedical High Technology, 1985 Conference, Ohio State University, Nov. 13-15, 1985.

Antiplatelet Actions of Cyclic and Aci-Reductone Analogs of Clofibric Acid, Romstedt et al., The Pharmacologist, 24 214 (Jul. 31, 1985).

METHOD FOR IMPROVING INTERLEUKIN-2 ACTIVITY USING ACI-REDUCTONE COMPOUNDS

BACKGROUND OF THE INVENTION

The present invention relates generally to the use of aci-reductone compounds to improve lymphokine activated killer (LAK) cytotoxicity and to the pharmaceutical use of such aci-reductone compounds in the treatment of cancer.

The invention further relates to a method for improving interleukin-2 (IL-2)-induced lymphocyte-killing of cancer cells in a patient having cancer by administering to a patient having cancer at least one aci-reductone compound containing a —C(OH)=C(OH)—C=O redox functionality or a physiologically acceptable salt thereof.

It is know that arachidonic acid (AA) metabolites and reactive oxygen species (ROS) suppress interleukin (IL-2) antitumor activity and mediate IL-2 toxicity. The present invention shows that aci-reductones, a family of synthetic compounds which inhibit AA and ROS metabolism, can improve IL-2 antitumor efficacy and lessen IL-2 toxicity.

IL-2 is an important mediator of the immune response. Of particular significance to cancer therapy is the capacity of IL-2 to generate cytotoxic lymphocytes. LAK cells are predominantly IL-2 activated natural killer (NK) cells which are capable of lysing tumors resistant to NK cells.

It is known that incubation of human peripheral blood mononuclear cells (PBMC) with interleukin-2 (IL-2) induces a population of highly tumoricidal lymphocytes. This phenomenon is referred to as LAK activity as described in Rosenburg, Adoptive immunotherapy of cancer using lymphokine activated killer cells and recombinant interleukin-2, in DeVita VT, Hellman S, Rosenberg SA (eds.): Important Advances in Oncology. Philadelphia: Lippincott, 1986, pp. 55–91. The precursor of the effector cells may be heterogeneous, but most of the activity appears to originate from IL-2 activation of natural killer (NK) cells as described in Ortaldo et al., Lymphokine activated killer cells: Analysis of progenitors and effectors. *J. Exp. Med.* 164:1193, 1986; and Philips et al., Dissection of the lymphokine activated killer phenomenon. *J. Exp. Med.* 161:814, 1986. IL-2, alone or with the adoptive infusion of LAK cells, has demonstrated antitumor activity in vivo. Although a wide spectrum of tumors are sensitive in vitro, most tumors have not been completely responsive in vivo. The best results in clinical trials have been with melanoma and renal cell carcinoma. Since promising responses have been observed in patients with tumors for which there are no effective chemotherapies, there is considerable interest in developing new IL-2 therapies. However, IL-2 regimens have also been toxic, inducing inflammatory responses such as fever and chills, and the capillary leak syndrome characterized by extravasation of plasma into tissues, hypotension, and multiple organ dysfunction. Most studies suggest that IL-2 toxicity results indirectly though the effects of proinflammatory cytokines such as tumor necrosis factor (TNF) and IL-1.

It is now believed that a number of mediators may be involved in the abrogation of IL-2 antitumor activity and in IL-2 toxicity. Several lines of evidence implicate a role for AA metabolites and ROS, which are both important mediators of the immune responses.

Metabolism of AA is by two basic pathways: (1) the cyclooxygenase pathway which leads to prostaglandin and thromboxane and (2) the lipoxygenase pathway which leads to leukotrienes and lipoxins. Products of both pathways have immunomodulatory effects. ROS having immunodulatory effects include superoxide anion ($O_2^-$), hydrogen peroxide ($H_2O_2$), hydroxyl radical, products of lipid peroxidation, and myeloperoxidase-halide-$H_2O_2$ products. The major source of AA metabolites and ROS relevant to cytoxic lymphocyte activity are phagocytes; tumors may also be important sources.

In particular, IL-2 has been shown to induce the production of AA and ROS metabolites as described in Parker et al., Formation of $TxB_2$ and hydroxyarachidonic acids in purified human lymphocytes in the presence and absence of PHA. *J. Immunol.* 122:1572, 1979; Remick et al., Stimulation of prostaglandin $E_2$ and thromboxane $B_2$ production by human monocytes in response to interleukin-2. *Biochem. Biophys. Res. Commun.* 147:86, 1987; Bermudez, Tumor necrosis factor, alone or in combination with IL-2, but not IFN-gamma, is associated with macrophage killing of *Mycobacterium avium* complex, *J. Immunol.* 140:3006–3013, 1988; Frasier-Scott et al., Influence of natural and recombinant interleukin-2 on endothelial cell arachionate metabolism, *J. Clin. Invest.* 82:1877–1883, 1988; Tilden et al., Interleukin-2 augmentation of interleukin-1 and prostaglandin $E_2$ production; *J. Leuk. Biol.* 45:474–478, 1989; Valitutti et al., The expression of functional IL-2 receptor on activated macrophage depends on the stimulus applied, *Immunology* 67:44–50, 1989; and, Klausner et al., The rapid induction by interleukin-2 of pulmonary microvascular permeability, *Ann. Surg.* 209:119–128, 1989. The suppressive effects of the cyclooxygenase product of AA, prostaglandin (PG) $E_2$, on lymphocyte cytotoxicity have been well-established by Chouaib et al., Prostaglandins E as modulators of the immune response, *Lymphokine Res.* 7:237–245, 1988. Further prostaglandin $E_2$ ($PGE_2$) released from macrophages from tumor-bearing mice has been shown to suppress LAK activity by Parhar et al., Prostaglandin $E_2$-mediated inactivation of various killer lineage cells by tumor bearing host macrophages, *J. Leuk. Biol.* 44:474–484, 1988. $PGE_2$ also down-regulates IL-2 receptors, blocks IL-2 production, and induces suppressor cells as shown by Parhar et al, supra; Lala et al., Cure of B16F10 melanoma lung metastasis in mice by chronic indomethacin therapy combined with repeated rounds of interleukin-2: characteristics of killer cells generate in situ, *Cancer Res.* 48:1072–1079, 1988; Rappaport et al., Prostaglandin $E_2$ inhibits the production of human interleukin-2. *J. Exp. Med.* 155:943–948, 1982; Rogers et al., Suppression of B-cell and T-cell responses by the prostaglandin synthesis-dependent suppressor (PITS), *Cell Immunol.* 66:269, 1982. Indomethacin, a specific inhibitor of cyclooxygenase has been shown to enhance LAK generation and IL-2 antitumor activity in mice by Lala, et al. supra. However, cyclooxygenase inhibitors, such as indomethacin and ibuprofen, have not been shown to modify tumor or immune responses in cancer patients receiving IL-2 therapy, as described in Sosman et al., Repetitive weekly cycles of interleukin-2. II. Clinical and immunologic effects of dose, schedule, and addition of indomethacin. *J. Natl. Cancer Inst.* 80:1451–1461, 1988; Eberlein et al., Ibuprofen causes reduced toxic effects of interleukin-2 administration in patients with metastatic cancer; *Arch. Surg.* 124:542-547, 1989. Reactive oxygen species ROS, such as superoxide anion ($O_2^-$), have been shown to inhibit NK activity by Seaman et al., Suppression of natural killing in vitro by monocytes and polymorphonuclear leukocytes. Requirements of reactive metabolites of oxygen. *J. Clin. Invest.* 69:876-888, 1982 and Lipsky, Immunosuppression by D-penicillamine in vitro:inhibition of human T lymphocyte proliferation by copper-or ceruloplasmin- dependent generation of hydrogen peroxide and protection by monocytes. *J. Clin. Invest.* 73:53-65, 1984. However, the effects of ROS on LAK cytotoxicity and whether ROS scavengers improve IL-2 antitumor activity in vivo have not been established. It is to be noted that patients responding to IL-2/LAK therapy had higher base-line levels of the ROS scavenger, ascorbic acid, and recovered more rapidly from IL-2 induced depletion of ascorbic acid than did non-responders, as described in Marcus et al., Severe hypovitaminoisis C occurring as the result of adoptive immunotherapy with high dose interleukin-2 and lymphokine activated killer cells. *Cancer Res.* 47:4028-4212, 1987.

Aci-reductone compounds are a family of synthetic compounds that contain the moiety: —C(OH)=C(OH)—C=O and are discussed in Witiak et al., Hypocholesterolemic and aggregatory properties of 2-hydroxytetronic acid redox analogues and their relation to clofibric acid. *J. Med. Chem.* 25:90-93, 1982; Witiak et al., Synthetic aci-reductones: 3,4-dihydroxy-2H-1-benzopyran-2-ones and their cis and trans 4a, 5, 6, 7, 8, 8a-hexahydro diastersomers. Antiaggregatory, antilipemic, and redox properties compared to those of the 4-substituted 2-hydroxytetronic acids, *J. Med. Chem.* 31:1437-1445, 1988; and Witiak et al., Comparative antiaggregatory activity in human platelets of a benzopyranone aci-reductone, clofibric acid, and 2,3-dihydrobenzofuran analogue. *J. Med. Chem.* 29:2170-2174, 1986. Possessing the same redox functionality found in ascorbic acid, aci-reductones can function as scavengers of ROS in vivo. In addition, aci-reductone compounds can also inhibit oxidizing enzymes involved in AA metabolism by serving as alkyl and aryl carboxylic acid mimics at the metal containing active sites.

It is shown herein that due to their capacity to affect both AA and ROS metabolism the aci-reductone compounds can improve IL-2-induced LAK generation.

SUMMARY OF THE INVENTION

One aspect of the present invention relates to aci-reductone compounds which function both as inhibitors of AA metabolism and as scavengers of ROS, to improve generation of IL-2-induced LAK activity. aci-Reductones belonging to the 4-substituted-2-hydroxytetronic acid systems improve the generation of LAK activity from IL-2-treated human peripheral blood mononuclear cells (PBMC) approximately 4-fold. aci-Reductones belonging to the 6-or 7- mono- or bis-substituted 3,4-dihydroxy-2H-1-benzopyran-2-one systems improve LAK generation approximately 2-fold. This improvement is comparable to that produced by indomethacin with superoxide dismutase plus catalase and is comparable to the improvement produced by depleting PBMC of monocytes. aci-Reductones completely suppressed the production of prostaglandin $E_2$ from PBMC in response to IL-2 and partially suppressed superoxide anion production. Daudi cell proliferation, lymphocyte subset proliferation and monocyte viability were not affected. No improvement in LAK activation was observed when PBMC depleted of monocytes were exposed to IL-2 and aci-reductones.

In a composition aspect, the present invention encompasses novel pharmaceutical compositions comprising an aci-reductone compound belonging to the 4-substituted-2-hydroxytetronic acid systems or the 6- or 7- mono- or bis-substituted-3,4-dihydroxy-2H-1-benzopyran-2-one systems, together with a physiologically acceptable carrier or excipient, in an amount sufficient to have lymphokine activated killer activites in an animal or human patient. The present invention is applicable to the treatment of cancers which respond to interleukin-2 therapies.

BRIEF DESCRIPTION OF THE FIGURES

FIGS. 3A and 3B are graphs showing the effects of aci-reductones (compounds 2 and 5 as shown in FIG. 2) on LAK activation from PBMC (FIG. 3A) and PBL (FIG. 3B) compared to the effects of indomethacin (INDO), flavone acetic acid (FAA), and coumarin (COUM); data represent mean values from 3 donors.

DESCRIPTION OF THE INVENTION

Figure 1A:
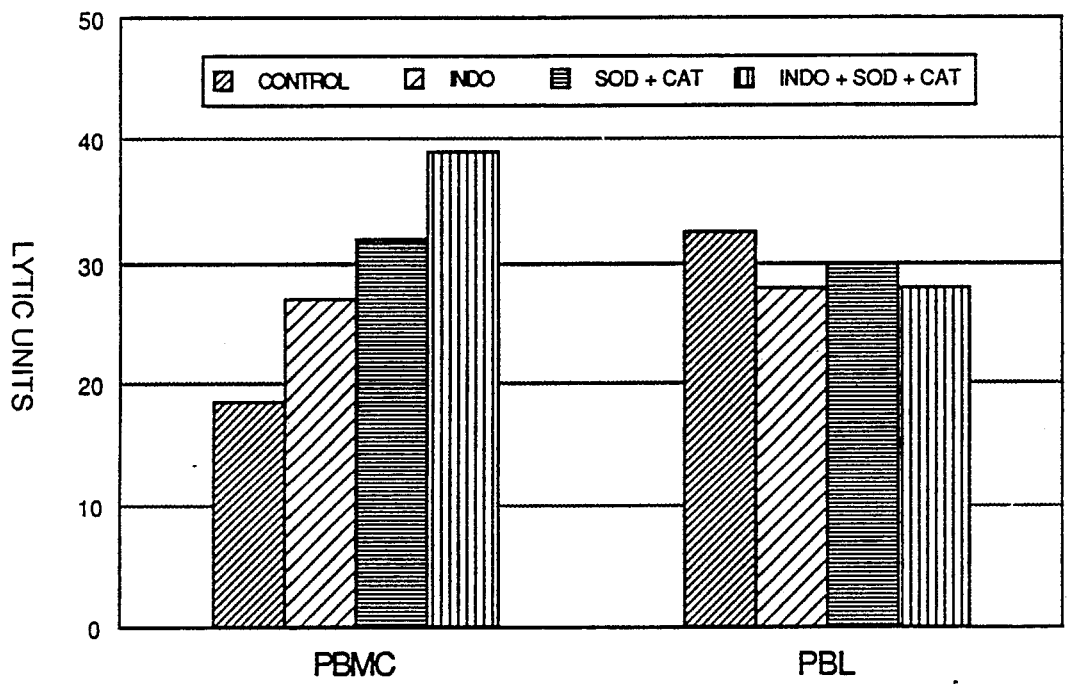
FIGS. 1A and 1B are graphs showing the effects of a control, indomethacin (INDO), superoxide dismutase and catalase (SOD+CAT), and indomethacin and superoxide dimutase and catalase (INDO+SOD+CAT) on the generation of LAK activity from peripheral blood mononuclear cells (PBMC) (FIG. 1A) and peripheral blood lymphocyte (PBL) (FIG. 1B) cultured at $10^6$ or $10^7$ cells/ml with IL-2 at 1000 U/ml for 4 days; data represent means values from cells obtained from 3 donors.

The present invention provides a method for improving interleukin-2 (IL-2) activity, specifically induced lymphocyte killing of cancer cells, by administering to an animal or human patient having cancer at least one aci-reductone compound containing a —C(OH)=C(OH)—C=O redox functionality.

aci-reductone compounds which function both as scavengers of ROS and as inhibitors of oxidizing enzymes involved in AA metabolism, improve LAK generation from PBMC cultured in vitro at high-density. The improvement in LAK generation is greater than that produced by other previously tested cyclooxygenase inhibitors and ROS scavengers. The improvement in LAK generation is comparable to that achieved by depleting PBMC of monocytes with phenylaniline methyl ester (PME). Monocytes appear to be the target of aci-reductone activity since generation of LAK activity from PBMC depleted of monocytes with PME is not improved. aci-Reductones did inhibit the production of an AA and ROS metabolite from PBMC exposed to IL-2 indicating that this capacity may be their mechanism of action.

aci-Reductones, which are currently evaluated for potential use in the therapy of thromboembolic disease, are more effective than previously tested inhibitors of AA metabolism and ROS scavengers in improving IL-2 antitumor activity. aci-Reductones have the potential to inhibit both cyclooxygenase and lipoxygenase as well as scavenger ROS. Specific inhibitors of cyclooxygenase, such as indomethacin and ibuprofen, increased the availability of AA as a substrate for lipoxygenase. This increased availability of AA leads to the formation of leukotrienes and lipoxins, AA metabolites which have the potential to inhibit cytotoxic lymphocyte activity as discussed in Ramstedt et al., Action of novel eicosanoids lipoxin A and B on human natural killer cell cytotoxicity: effects on intracellular cAMP and target cell binding, *J. Immunol.* 135:3434, 1985 and Rola-Pleszczynski et al., Leukoptriene B4 induces human suppressor lymphocytes,*Biochem. Biophys. Res. Commun.* 108:1531, 1982.

aci-Reductone compounds are relatively more lipophilic than ascorbic acid. Lipophilicity varies as a function of the 4-substituent in 4-aryl-2-hydroxytetronic acids designed to inhibit cyclooxygenase as well as scavenge activated oxygen and other radials. The various aci-reductones may concentrate and/or penetrate the nonperfused areas present in tumors. Tumor cells are potential sources of AA and ROS metabolites as discussed in Lala et al. supra, and in Bizer et al., Superoxide dismutase and superoxide radical in Morris hepatomas, *Canc. Res.* 40:3686-3693, 1980.

IL-2 therapies have also been limited by toxicity IL-2 most notably produces the capillary leak syndrome which leads to massive fluid retention and hypotension. AA metabolites have been implicated in mediating this toxicity, and aci-reductones are likely beneficial in abrogating this IL-2 toxicity, which is discussed in Klausner et al., supra, and in Klausner et al., Role of thromboxane in interleukin-2 induced lung injury in sheep, *Cancer Res.* 49:3542-3549, 1989. It is important that agents used in conjunction with IL-2 do not increase the already considerable IL-2 clinical toxicity. Flavone acetic acid (FAA) causes significant hypotension as discussed in Grever et al., A phase I investigation of flavone acetic acid (NSC347512). *Proc Am. Soc. Clin. Oncol.* 7:62, 1988. Indomethacin aggravates IL-2 fluid retention as discussed in Sosman, et al., supra. Also, of critical importance is that agents not be toxic to the cytotoxic lymphocyte. Whereas coumarin improves LAK generation, higher concentrations of coumarin, in contrast to aci-reductones, diminishes LAK generation suggesting that they are toxic to LAK cells. Animal studies have also demonstrated that aci-reductones are very well-tolerated nor does compound 2 stimulate perixosme proliferation.

The invention provides for the use of aci-reductone compounds of the general formulas I and II and

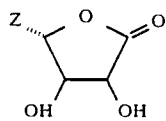

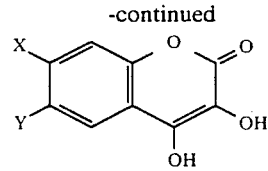

wherein Z is selected from the group comprising $C_1$–$C_8$ straight or branched alkyl or alkoxy-substituted alkyl group, $C_3$–$C_8$ cycloaliphatic group or spiro alkyl group, a halo-$C_1$–$C_8$ alkyl group, aryl or aralkyl group, or substituted aryl or aralkyl group including those of the formula

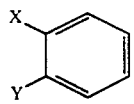

wherein X and Y are as described infra; and, wherein X and Y are independently selected from the group comprising H, OH, halogen, a $C_1$–$C_8$ straight or branched alkyl or alkoxy group, phenyl, phenyloxy or phenyl substituted by a $C_1$–$C_8$ straight or branched alkyl, alkoxy or halogen, or wherein X, Y is $OCH_2O$.

As used herein, the term "alkyl" means straight- or branched-chain saturated aliphatic hydrocarbon groups preferably containing 1–8 carbon atoms. Representative of such groups are methyl, ethyl, isopropyl, butyl, pentyl, hexyl and the like.

The term "cycloaliphatic" means a lower alkyl hydrocarbon group which is closed to form a ring structure. Preferred cycloaliphatic groups are saturated lower alkyl hydrocarbon ring structures containing from 3–6 carbon atoms. Especially-preferred are saturated groups containing 4–6 carbon atoms and bonded so as to form 4,4-spiro species.

The term "alkoxy" means a lower alkyl group attached to the remainder of the molecule by oxygen. Examples of alkoxy are methoxy, ethoxy, propoxy, isopropoxy and the like.

The term "aryl" means an organic, aromatic radical derived by the removal of one atom (e.g., phenyl) which can be substituted or unsubstituted by one or more lower alkyl groups (e.g., tolyl).

The term "aralkyl" means a group in which an alkyl atom is substituted by an aryl group wherein aryl and alkyl are as defined above. Examples of aralkyl are benzyl and phenethyl.

The term "substituted aryl or aralkyl" means araryl or aralkyl group substituted by a halogen, lower alkyl, alkoxy, aromatic or heteroaromatic group. Examples include: substituted phenyls (ortho, meta or para) i.e., disubstituted 2,3-dichlorophenyl-, 2,4-dichlorophenyl-; and thiopene.

The invention provides pharmaceutical compositions comprising the aci-reductone compounds of the general formulas I and II above, and the physiologically acceptable salts thereof (such as, for example, $Na^+$, $K^+$, $NH_4^+$) together with a physiologically acceptable carrier or excipient.

The aci-reductone compounds of the invention are inhibitors of oxidizing enzymes involved in arachidonic acid (AA) metabolism and scavengers of reactive oxygen species (ROS) and are useful in the treatment or prevention of various cancers. The invention accordingly further provides aci-reductone compounds of the general formulas I and II and their physiologically acceptable salts for use in the therapy or prophylaxis of cancers which respond to interleukin-2 therapy.

The compositions of the invention may be formulated in a conventional manner, optionally together with one or more other active ingredients, for administration by any convenient route for example for oral, intravenous or intramuscular administration.

For oral administration, the pharmaceutical composition may take the form of, for example, tablets, capsules, powders, solutions, syrups or suspensions prepared by conventional means with physiologically acceptable excipients.

The compounds may be formulated for intravenous or intramuscular administration in dry form for reconstitution before use, or as a sterile solution or suspension.

A proposed daily dose based on similar pharmacokinetic parameters to 4-(4-chlorophenyl)-2-hydroxytetronic acid (CHTA) for administration to man is 10 to 25 to mg/kg, for example, 1 gm daily to 70 kg., which may be conveniently administered in 1 to 3 doses per day. The precise dose administered will of course depend on the age and condition of the patient.

The aci-reductone compounds may be prepared by a number of processes. For example, the aci-reductone compounds of the general formula I above may be prepared according to the processes disclosed in the copending patent application, Witiak et al., Ser. No. 07/464,511 filed Jan. 12, 1990 and assigned to the same assignee as herein, which application is expressly incorporated herein by reference.

The aci-reductone compounds of the general formula II above may be prepared according to the processes disclosed in the Witiak et al., U.S. Pat. No. 4,845,121 issued July 4, 1989 and in the divisional application thereof, Ser. No. 07/360,526 filed June 2, 1989, which are expressly incorporated herein by reference.

Figure 2:
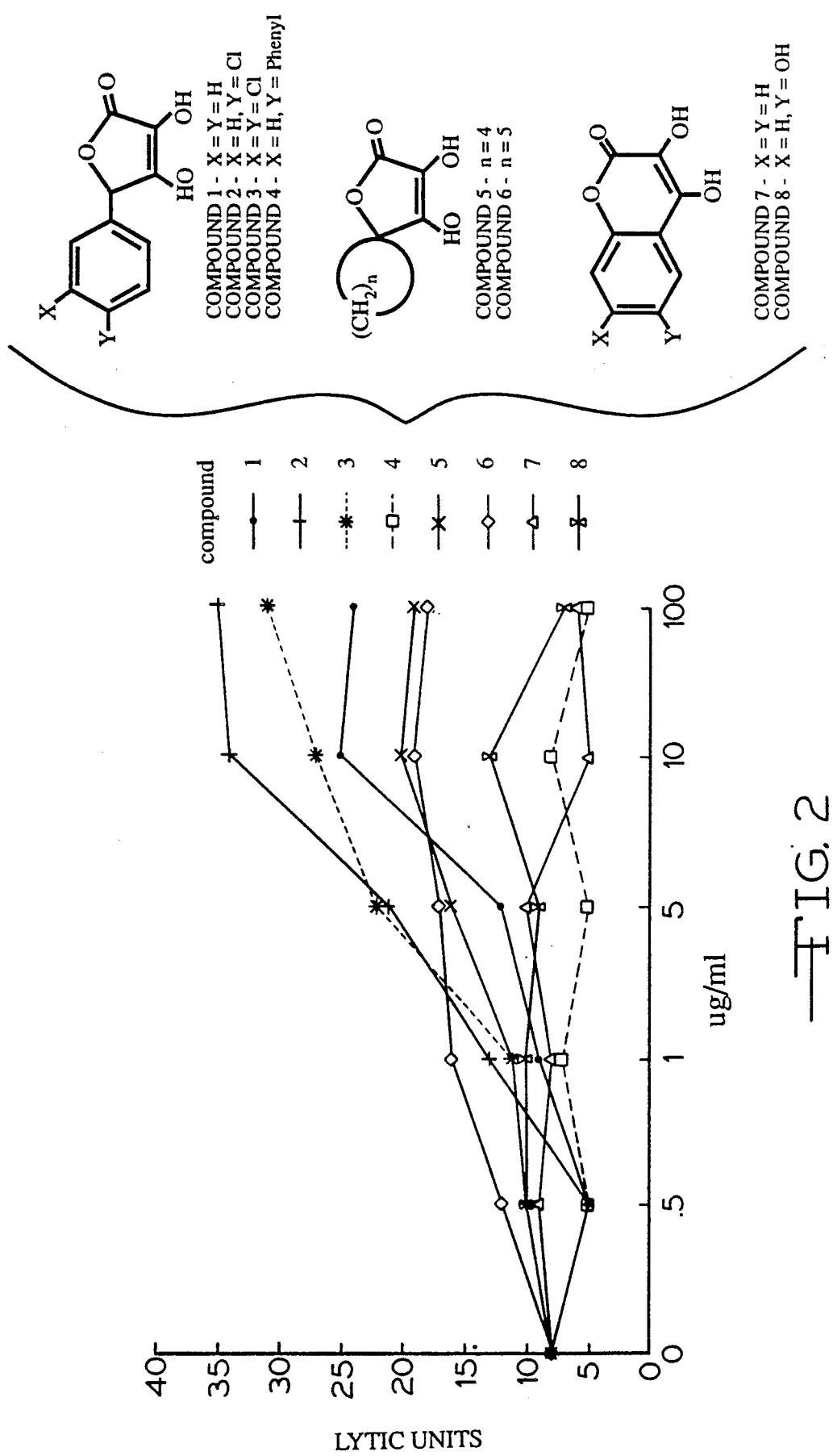
FIG. 2 is a graph showing the effects of aci-reductones on the generation of LAK activity from PBMC culture at $10^7$ cells/ml with IL-2 at 1000 U/ml for 4 days; the structures of the compounds depicted by the data in FIG. 2 are as shown; data represent means values from cells obtained from 4 donors.

Various compounds, as shown in FIG. 2, were screened. These include the 4-aryl-2-hydroxytetronic acids (compounds 1-4), the 4-spiroalkyl-2-hydroxytetronic acids (compounds 5 and 6), and the benzopyran-2-ones (compounds 7 and 8). Indomethacin (INDO) [1-(4-chlorobenzoyl)-5-methoxy-2-methyl-1H-indole-3-acetic acid] superoxide dismutase (SOD), catalase (CAT), and coumarin (COUM) [1,2-benzopyran-2-one] were purchased from Sigma Chemical Co., St. Louis, MO. Flavone acetic acid (FAA) [2-phenyl-8-(carboxymethyl)benzopyran-4-one] was obtained from the Division of Cancer Treatments, National Cancer Institute, Bethesda, MD.

Peripheral blood mononuclear cells (PBMC) were separated by density gradient centrifugation with Ficoll-Hypaque from peripheral blood collected from healthy volunteers. Peripheral blood lymphocyte (PBL) preparations were prepared by depleting PBMC of monocytes using phenylalanine methyl ester (PME) (Sigma Chemical Co.). PBMC were suspended at $5 \times 10^6$ cells/ml in RPMI 1640 (GIBCO), Grand Island, NY). PME was dissolved in RPMI, pH was readjusted to 7.4 with 10M NaOH, and the solution was sterilized by passage through a 0.22 um filter. The PBMC were incubated with 5 mM of PME in polypropylene 50 ml conical tubes (Falcon 2098; Falcon Labware, Lincoln Park, NJ) for 40 minutes at room temperature. The cells were washed with cold HBSS and resuspended. The lymphokine activated killer (LAK) culture media (CM) consisted of RPMI, 10% fetal calf serum, and 1% antibiotics (GIBCO), and 1000 U/ml interleukin-2 (IL-2) (Proleukin, Cetus, Emeryville, CA).

The LAK cytotoxicity was evaluated as follows: Standard 4-hour $^{51}Cr$ release assays were used to measure cytotoxicity using natural killer (NK) resistant Daudi cells as the tumor target. Daudi cells (2 to $10 \times 10^6$) were incubated with 100 uCi of $Na_2{}^{51}CrO_2$ (New England Nuclear, Boston, MA) in 0.4 ml of trisphosphate buffered saline for 1 hour at 37° C. The cells were washed 4 times with CM and were resuspended in CM at $10^5$/ml. Effector cells were suspended to various concentrations, and 0.1 ml was added to round bottomed microtiter plates (Flow Laboratories, McLean, VA). The $^{51}Cr$-labeled target cells were added to all wells in 0.1 ml and the plates were centrifuged at 200 g for 5 minutes. After 4 hours of incubation at 37° C., the plates were centrifuged again, and 0.1 ml of supernatant was removed from each well and counted in a gamma counter. Percent lysis was calculated from the formula: (experimental cpm − spontaneous cpm)/total cpm − spontaneous cpm). Data is expressed as percent lysis or in lytic units, the number of tumor target cells lysed × 100 by 8000 effector cells.

The production prostaglandin $E_2$ ($PGE_2$) was quantitated using a radioimmunoassay as described in Fertel R., et al., Formation of Antibodies to prostaglandino in the yolk of chicken eggs. *Biochem. Biophys. Res. Comm.*, 102:1028-1033 (1981).

The production of $O_2{}^-$ was quantitated according to the method of Pick et al., Rapid assays for the measurement of superoxide and hydrogen peroxide production by macrophages in culture using an automatic enzyme immunoassay reader. *J. Immunol. Methods* 46:211-226 (1981), which measures the oxidation of cytochrome c. Cytochrome c (80 uM) was added to the cultures. A control reaction consisting of the reaction mixture with 40 ug/ml of SOD was used. "Blank" wells were prepared without cells, with and without SOD. Reactions were allowed to proceed at 37° C. for 1 hour. After incubation, the absorbence (E) at 55 nm was measured on an automatic enzyme-linked immunosorbent assay reader. Absorbence was converted to nm $O_2{}^-$ produced by multiplying $E_{(550\ nm)}$ by $2.1 \times 10^4$/cm. Results are expressed as nm $O_2{}^-/10^7$/h.

Phenotyping of lymphocytes was accomplished using monoclonal antibody (MAB) and a fluorescence activated cell sorter (FACS). Lymphocytes were reacted with no MAB and with MAB versus NK (Leu 19, CD56), T helper (Leu 2a; CD4), and T suppressor (Leu 3a, CD8) and then with a fluorescenated anti-mouse antibody (Becton-Dickenson, Mountain View, CA) under condition recommended by the manufacturer. Percent fluorescent cells and fluorescent intensity was determined using an OrthoSystem 50H cytofluorograph.

Figure 1B:
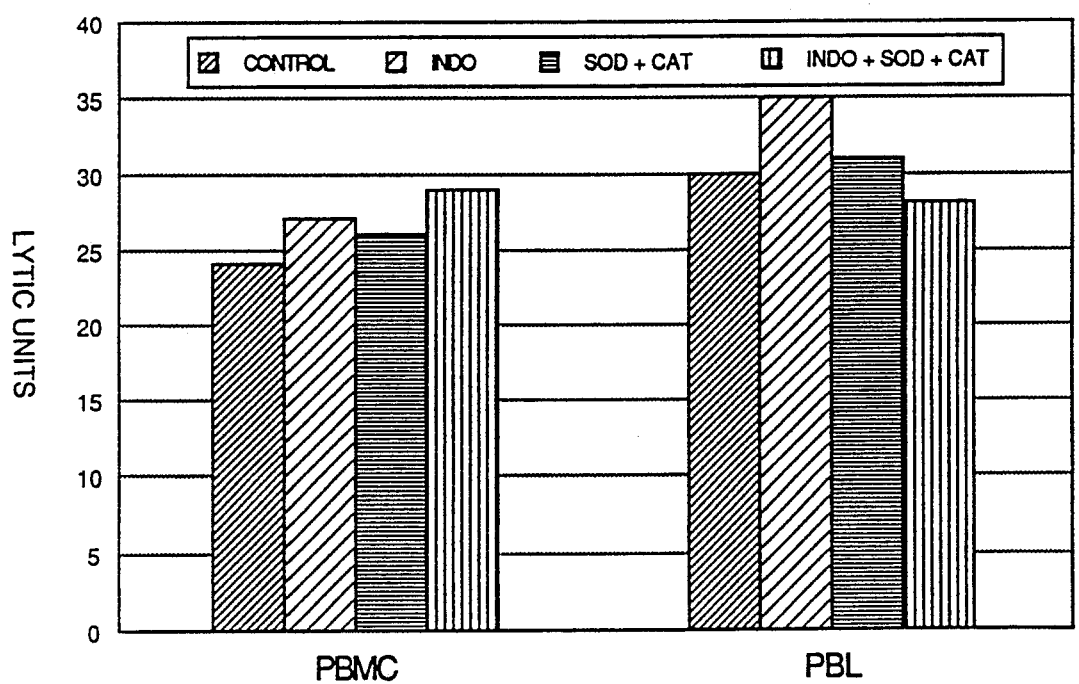

The evaluation of LAK activity at high density establishes the model system in which the effects of inhibitors of AA and ROS metabolism on LAK activation can be evaluated. Cell density is an important determinant in the activation of LAK cells from PBMC in vitro: culturing PBMC at densities > $10^6$ cells/ml reduces LAK activation. The production of AA metabolites and ROS by monocytes have been implicated in the suppression of LAK generation since depleting PBMC of monocytes improves LAK activation at high density, as discussed in Hoyer et al., Characterization and modulation of human lymphokine (interleukin-2) activated killer cell induction, *Cancer Res.* 46:2834-2838, 1986. It is noted that other mechanisms may also be important in the suppression of LAK activation by monocytes as discussed in Oshimi et al., Natural killer-mediated lysis of normal and malignant target cells and its regulation by monocytes, *J. Exp. Med.* 162:472-486, 1985; and, Roth et al., Inhibition of Lymphokine-activated killer cell function by human alveolar macrophages, *Cancer Res.* 49:4690-4695, 1989. Culturing PBMC at high density, i.e., >10$^6$ cells/ml, with IL-2 maximizes the suppressive effects of monocyte/macrophages and appears to be representative of in vivo LAK generation, since monocytes/macrophages in situ may be inhibitory. The LAK generation at cell densities of 10$^6$ and 10$^7$ cells/ml was investigated in the presence of a control, indomethacin (INDO), superoxide dimutase and catalase (SOD & CAT), and indomethacin, superoxide dimutase and catalase (INDO & SOD & CAT) in order to inactivate $O_2^-$ and to inactivate hydrogen peroxide. Both PBMC and PBL preparations were evaluated and the results are shown in FIG. 1A and 1B, respectively. This model provides evidence that AA and ROS metabolites are important factors in regulating LAK activation. Monocytes appear to be the site of activity since no improvement in high density LAK generation from PBL was noted. This evaluation supports the use of aci-reductones which affect both AA and ROS metabolism.

The effect of aci-reductones on the generation of LAK activity in vitro was evaluated. Screening studies were performed evaluating the effects of aci-reductones on LAK cell generation using the above high density model. In the first set of screening experiments, a range of concentrations of aci-reductones were tested for LAK generation from PBMC, as shown in FIG. 2. aci-Reductones belonging to the 4-aryl-2-hydroxytetronic acid systems, compounds 1-3 produced the greatest improvement in LAK activation. Maximal enhancement occurred in concentration ranges of 10 μg/ml. Improvement in LAK generation was also observed with aci-reductones of the 4-spiroalkyl-2-hydroxytetronic acid systems (compounds 5 and 6). No improvement was observed with the benzopyran-2-ones (compounds 7 and 8) nor with the phenylated 4-spiroalkyl-2-hydroxytretonic acid, compound 4.

Figure 3:
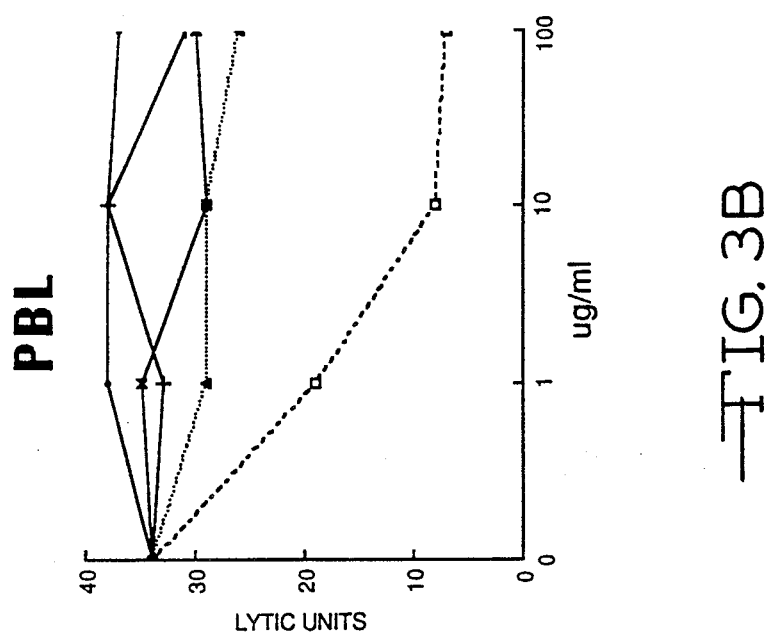
FIG. 3 shows the structural formulae of Coumarin, Indomethacin and Flavone acetic acid.
Figure 3:
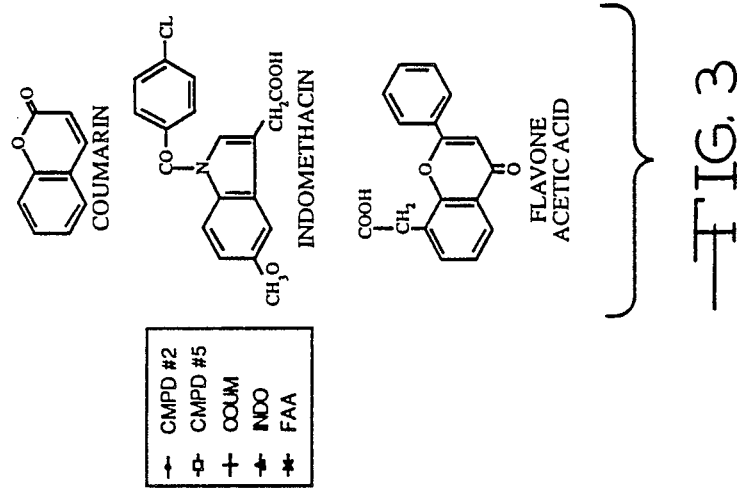
Figure 3:
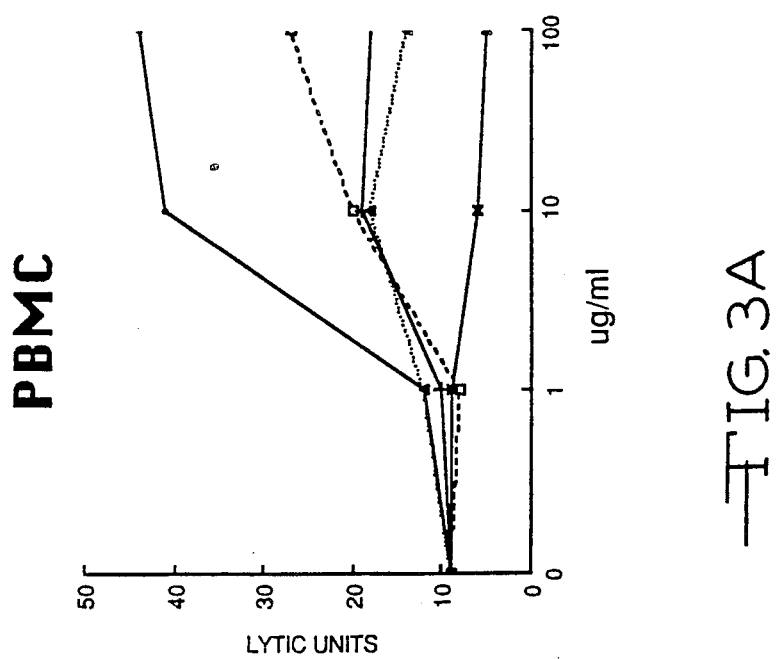

The effects of compounds 2 and 5 were compared to that produced by indomethacin, flavone acetic acid (FAA) and coumarin. It has been suggested by Urba et al., Enhancement of natural killer activity in human peripheral blood by flavone acetic acid, *J. Natl. Cancer Inst.* 80:521-525, 1988 that the capacity of FAA to inhibit cyclooxygenase may be important in its enhancement of IL-2 antitumor activity in mice. Further, coumarin has immunomodulatory and antitumor activity and has been shown to inhibit ROS generation by monocytes as discussed in Marshall et al., Effects of coumarin (1,2-benzopyrone) on lymphocyte, natural killer cell, and monocyte functions in vitro, *J. Biol. Response Mod.* 8:70-85, 1989. FAA and coumarin do not possess and aci-reductone moiety. The effects of aci-reductone compounds 2 and 5 on LAK activation from PBMC and PBL compared to the effects of indomethacin (INDO), flavone acetic acid (FAA) and coumarin (COUM) are shown in FIGS. 3A and 3B, respectively.

Figure 4:
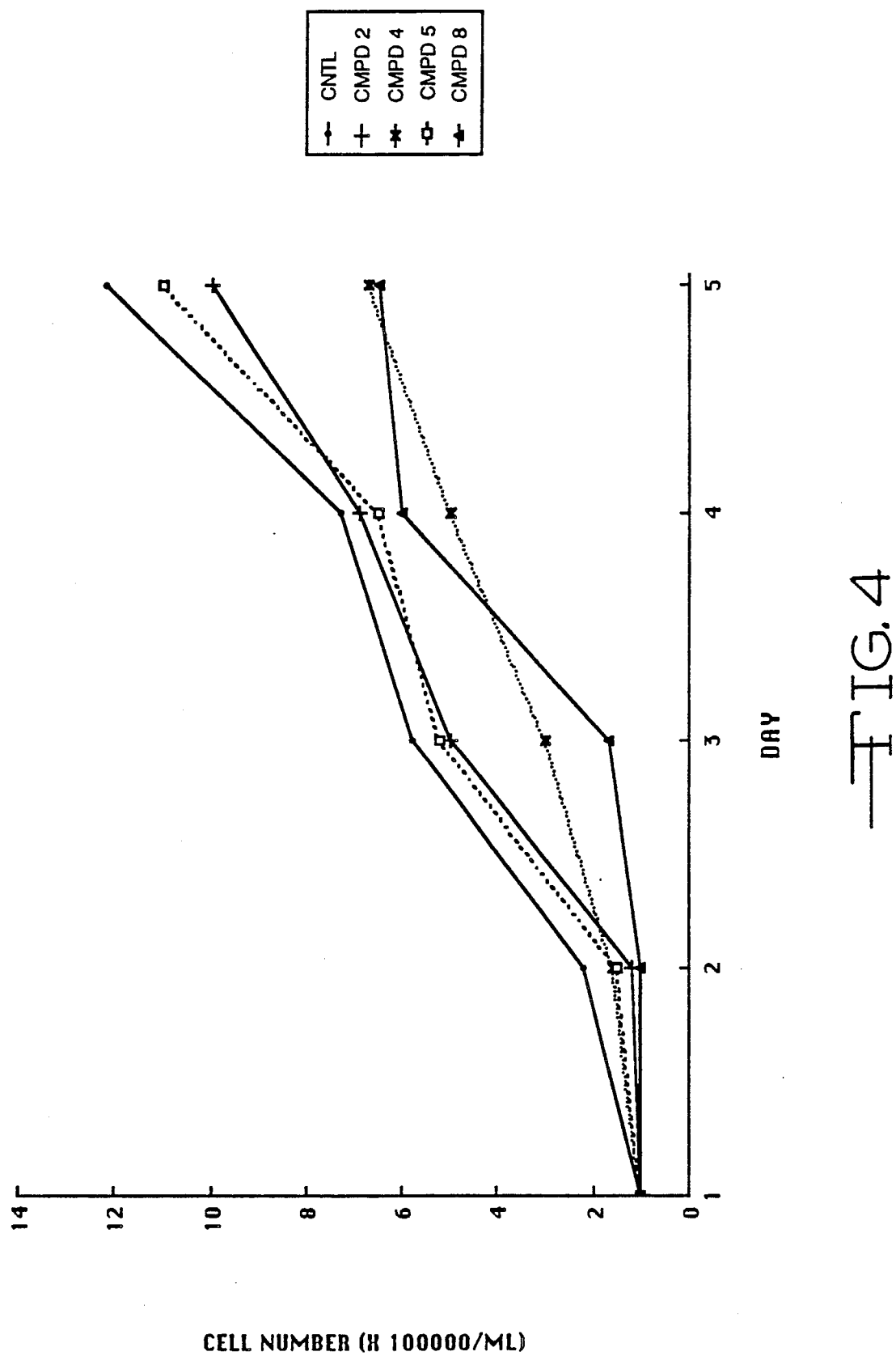
FIG. 4 is a graph showing the effect of aci-reductones on Daudi cell proliferation; Daudi cells ($10^5$/ml) were cultured without (CNTL) and with compounds 2, 4, 5, and 8 (10 ug/ml) for 5 days; cell number was quantitated using a hemocytometer and Trypan blue exclusion staining.

Whether the aci-reductone compounds themselves were directly toxic to tumor cells was determined versus the Daudi cells used in the LAK cytotoxicity assays. Cells were cultured at 10 ug/ml compounds 2, 4, 5, and 8. At this concentration, enhancement of LAK generation could be demonstrated. Viability was determined using by counting cell number using a hemocytometer and Trypan blue exclusion for 7 days of culture. The results are shown in FIG. 4. Compounds 2 and 5, aci-reductones that enhanced LAK generation, did not directly affect Daudi cell proliferation. Compounds 4 and 8, agents that did not enhance LAK generation, decreased Daudi cell proliferation.

Also evaluated was whether aci-reductones were directly toxic to monocytes. Differential counts of the PBMC preparations before and after exposure to compounds 2, 4, 5, and 8 did not vary.

It is known that LAK "expansion" is an important component of the IL-2 antitumor response as discussed in Mule et al, The antitumor efficacy of lymphokine activated killer cells and recombinant interleukin-2 in vivo, *J. Immunol.* 135:646, 1985. The effects of aci-reductones on the proliferation on various lymphocyte subsets using MAB and FACS were evaluated. The lymphocyte subsets evaluated included NK cells, T suppressor, and T helper cell. Although the aci-reductones tested enhanced LAK activation, they did not improve LAK expansion using PBMC and PBL preparations nor did they selectively affect the proliferation of any lymphocyte subset. The results are shown in Table 1 below.

PBMC and PBL preparations were cultured at 10$^7$ cells/ml for 5 days, resuspended, and cultured an additional 4 days in the absence (CNTL) or presence or absence of compound (CMPD) 2 and 5 (10 ug/ml) and indomethacin (INDO; 10 ug/ml). Lymphocyte subsets, T-helper (CD4), T-suppressor (CD8), and NK (CD56), were identified using MAB and FACS.

LAK expansion was determined as follows: The number of cells obtained after 9 days of culture under the experimental conditions divided by the number of cells initially cultured. The LAK activity was measured in LU-lytic units.

TABLE 1

The Effects of aci-Reductones on Lymphocyte subset proliferation and LAK Expansion

| | LAK Expansion (Fold Increase) | LAK Activity (LU) | CD4 (%) | CD8 (%) | CD56 (%) |
|---|---|---|---|---|---|
| | | PBMC | | | |
| CNTL | 1.8 | 11 | 43 | 26 | 14 |
| PBMC + CMPD 2 | 2.1 | 38 | 43 | 28 | 17 |
| PBMC + CMPD 5 | 2.1 | 19 | 41 | 23 | 13 |
| PBMC + INDO | 2.2 | 30 | 39 | 26 | 13 |
| | | PBL | | | |
| CNTL | 3.9 | 39 | 46 | 23 | 19 |
| PBL + CMPD 2 | 4.1 | 38 | 44 | 29 | 18 |
| PBL + CMPD 5 | 3.9 | 29 | 39 | 29 | 16 |
| PBL + INDO | 4.0 | 35 | 48 | 27 | 15 |

The effect of aci-reductones on AA and ROS metabolism was evaluated. Interleukin-2 (IL-2) has been shown to increase the production of PGE$_2$ from PBMC exposed to IL-2 in vitro as discussed in Tilden et al., supra. The capacity of compounds 2 and 5 to affect the induction of prostaglandin E$_2$ (PGE$_2$) in response to IL-2 from PBMC culture at high density was evaluated. In addition, the effects of compounds 2 and 5 on the generation of $O_2^-$ from PBMC in response to IL-2 and in response to phorbol myristate acetate (PMA) were evaluated. Table 2 below shows that both compounds 2 and 5 completely inhibited the production of $PGE_2$ and that the production of the ROS, $O_2^-$ was only partially suppressed.

TABLE 2

The Effect of aci-Reductones on $PGE_2$ and $O_2^-$ Production

| | $PGE_2$(ng/ml) | $O_2^-$(nM/$10^7$ cells/h) |
|---|---|---|
| PBMC | 0 | 153 |
| PBMC + IL-2 | 72 | 403 |
| PBMC + IL-2 + CMPD 2 | 0 | 295 |
| PBMC + IL-2 + CMPD 5 | 0 | 300 |
| PBMC + IL-2 + INDO | 0 | 310 |
| PBMC + PMA | not done | 540 |
| PBMC + PMA + CMPD 2 | not done | 307 |

PBMC were cultured at $10^7$ cells/ml with and without IL-2 (1000 U/ml) without and with aci-reductone compounds (CMPD) 2 and 5; 10 μg/ml), indomethacin (INDO; 10 μg/ml), and phorbol myristate acetate (200 nM) for 72 hours to determine $PGE_2$ production and for 1 hour to determine $O_2^-$ production. Data represent mean values from triplicate assays using cells from 1 donor.

Although the invention has been illustrated by the preceding examples, it is not to be construed as being limited to the materials disclosed therein; but rather the invention is directed to the generic area as hereinbefore disclosed. Various modification and embodiments can be made without departing from the spirit or scope thereof.

We claim:

1. A method for improving interleukin-2 induced lymphocyte killing of cancer cells which respond to interleukin-2-therapy comprising administering to a patient having cancer undergoing interleukin-2-therapy an effective amount of at least one aci-reductone compound containing a —C(OH)=C(OH)—C=O redox functionality or a physiologically acceptable salt thereof together with a physiologically acceptable carrier or excipient wherein the aci-reductone compound comprises a 4-substituted-2-hydroxytetronic acid compound having a general formula

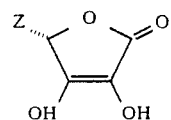

wherein Z is of the formula

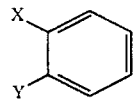

wherein X and Y are independently selected from the group consisting of H, OH, halogen, $C_1-C_8$ straight or branched alkyl or alkoxy group, phenyl, phenyloxy or phenyl substituted by $C_1-C_8$ straight or branched alkyl, alkyoxy or halogen.

2. The method of claim 1 in which the 4-substituted-2-hydroxytetronic acid compound comprises a compound of the formula

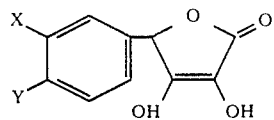

wherein X=H and Y=Cl.

3. A method for improving interleukin-2 induced lymphocyte killing of cancer cells which respond to interleukin-2-therapy comprising administering to a patient having cancer undergoing interleukin-2-therapy an effective amount of a 4-substituted-2-hydroxytetronic acid compound of the formula

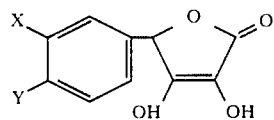

wherein X=Y=H; X=H, Y=Cl; X=Y=Cl; or X=H, Y=phenyl.

* * * * *